United States Patent
Muramatsu et al.

(10) Patent No.: US 6,465,477 B1
(45) Date of Patent: Oct. 15, 2002

(54) STABLE PHARMACEUTICAL COMPOSITION

(75) Inventors: Toyojiro Muramatsu, Shizuoka (JP); Katsumi Mashita, Fuji (JP); Yasuo Shinoda, Shizuoka (JP); Hironori Sassa, Numazu (JP); Hiroyuki Kawashima, Fuji (JP); Yoshio Tanizawa, Okayama (JP); Hideatsu Takeuchi, Fuji (JP)

(73) Assignees: Kowa Company, Ltd., Aichi-Ken (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/436,789

(22) Filed: Nov. 8, 1999

Related U.S. Application Data

(63) Continuation-in-part of application No. 08/894,279, filed on Aug. 18, 1997, now abandoned.

(51) Int. Cl.[7] .................. A61K 31/435; A61K 31/44; A61K 31/19

(52) U.S. Cl. ................. 514/277; 514/306; 514/569; 514/970

(58) Field of Search .................. 514/256, 277, 514/306, 415, 569, 970

(56) References Cited

U.S. PATENT DOCUMENTS

| | | | | |
|---|---|---|---|---|
| 5,302,604 A | * | 4/1994 | Byrne et al. | 514/338 |
| 5,356,896 A | * | 10/1994 | Kabidi et al. | 514/256 |

* cited by examiner

*Primary Examiner*—Frederick Krass
*Assistant Examiner*—Donna Jagoe
(74) *Attorney, Agent, or Firm*—Peter F. Corless; Christine C. O'Day; Edwards & Angell, LLP

(57) ABSTRACT

Disclosed is a pharmaceutical composition comprising (E)-3,5-dihydroxy-7-[4'-4"-fluorophenyl-2'-cyclopropyl-quinolin-3'-yl]-6-heptenoic acid, or its salt or ester, of which the aqueous solution or dispersion has pH of from 6.8 to 8. The composition has good time-dependent stability and has no change in its outward appearance even after having been stored long.

15 Claims, 2 Drawing Sheets

STABLE PHARMACEUTICAL COMPOSITION

The present application is a continuation-in-part of U.S. application Ser. No. 08/894,279 filed Aug. 18, 1997, now abandoned.

FIELD OF THE INVENTION

The present invention relates to a pharmaceutical composition with high stability and, more precisely, to a pharmaceutical composition comprising an HMG-CoA reductase inhibitor of which the stability varies depending on pH, especially (E)-3,5-dihydroxy-7-[4'-4"-fluorophenyl-2'-cyclopropyl-quinolin-3'-yl]-6-heptenoic acid, or its salt or ester.

BACKGROUND OF THE INVENTION

It is known that 7-substituted-3,5-dihydroxy-6-heptenoic acids of a general formula:

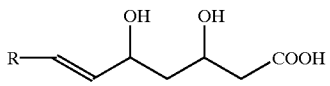

wherein R represents an organic group, have HMG-CoA reductase-inhibiting activity, and are useful as medicines for hyperlipemia and also as medicines for atherosclerosis (see U.S. Pat. Nos. 4,739,073, 5,001,255, 4,751,235, 4,804,679, EP-B-304,063).

However, these 7-substituted-3,5-dihydroxy-6-heptenoic acids are unstable at low pH, and require some particular means for formulating them into preparations. A means of formulating them along with an alkaline medium, such as calcium carbonate or sodium carbonate, into preparations with pH of 8 or higher (see U.S. Pat. No. 5,356,896), and a means of formulating them along with a basic agent, such as magnesium oxide or sodium hydroxide, into preparations with pH of 9 or higher (see EP-B-336,298) have been proposed.

(E)-3,5-dihydroxy-7-[4'-4"-fluorophehyl-2'-cyclopropyl-quinolin-3'-yl]-6-heptenoic acid (hereinafter this may be referred to as NK-104) to be represented by a structural formula:

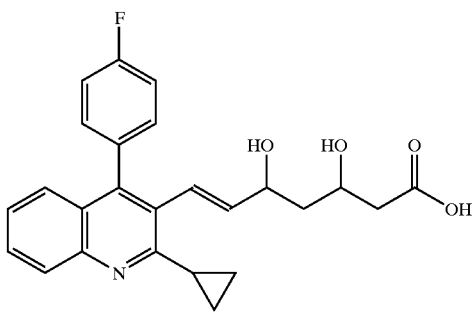

or its salt or ester is one of HMG-CoA reductase inhibitors that are represented by the above-mentioned general formula, and is known to be useful as a medicine for hyperlipemia and also as a medicine for atherosclerosis (see EP-B-304,063). NK-104 is also unstable at low pH, and many difficulties have been encountered in formulating it into preparations.

It has been reported that these HMG-CoA reductase inhibitors are formulated into preparations with pH 8 or higher, desirably pH 9 or higher, but unexpectedly, it has been found that NK-104 and its salts and esters are still unstable even within a high pH range.

Therefore, preparations comprising NK-104 or its salt or ester, if formulated in conventional manners, have low time-dependent stability, and are problematic in that their outward appearance changes with the lapse of time. Given the situation, the development of stable preparations comprising it is desired.

SUMMARY OF THE INVENTION

We the present inventors have variously studied in order to obtain stable pharmaceutical compositions comprising NK-104 and, as a result, have found unexpectedly that NK-104 is stable within a relatively low pH range. On the basis of this finding, we have completed the present invention.

Furthermore, we investigated decomposition products of NK-104 and fluvastatin in an aqueous solution of pH3. The decomposition product of NK-104 was found in small quantity and consisted only of the lactonized form of NK-104 (see FIG. 1). On the other hand, decomposition products of fluvastatin were found in relatively large quantities consisting of more than one type of products which are believed to include an optical isomer and a lactonized form of fluvastatin (see FIG. 2). These results showed that the decomposition pattern and stability of NK-104 and fluvastatin were different in the same pH.

In addition, we have further found that, if a basic substance is added to a pharmaceutical composition comprising NK-104 in such a manner that the aqueous solution or dispersion of the composition may have pH of from 6.8 to 8, the composition is stable.

An object of the present invention is to provide a pharmaceutical composition comprising NK-104, or its salt or ester, of which the aqueous solution or dispersion has pH of from 6.8 to less than 8, preferably has pH of from 6.8 to 7.8.

The active ingredient of the composition of the present invention is NK-104 to be represented by the above-mentioned structural formula. The configuration in this substance, NK-104 is not specifically defined herein. In addition, NK-104 may be in any form of its salts and esters. The salts include, for example, sodium salt, potassium salt and calcium salt. Preferred is calcium salt of NK-104.

DETAILED DESCRIPTION OF THE INVENTION

Figure 1:
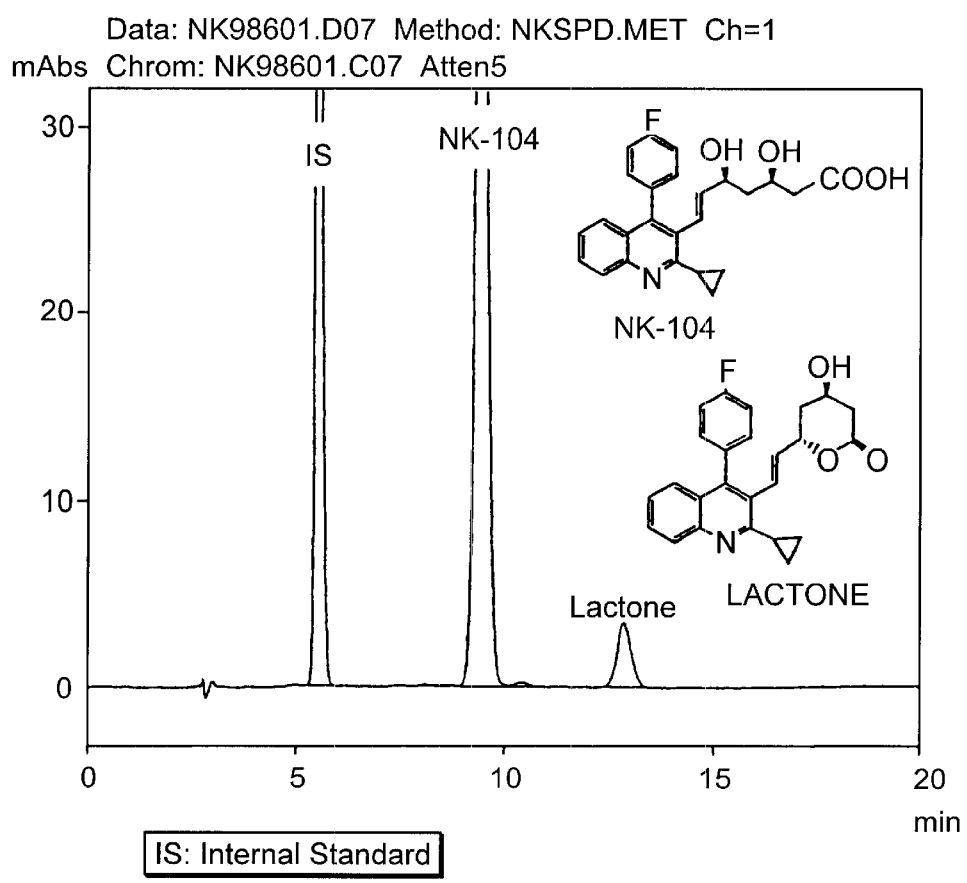
FIG. 1 is a histogram of NK-104 decomposition products analyzed by HPLC.

The pH as referred to herein indicates the pH value to be determined in such a manner that a unit dose of a solid preparation comprising NK-104 or its salt or ester is sampled and dissolved or dispersed in from 1 to 10 ml of pure water, and the pH of the resulting aqueous solution or dispersion is measured.

A basic substance may be added to the pharmaceutical composition comprising NK-104 to control the pH of the composition, which may be any of antacids and pH regulators including, for example, antacids such as magnesium aluminometasilicate, magnesium aluminosilicate, magnesium aluminum silicate, magnesium aluminate, dry aluminum hydroxide, synthetic hydrotalcite, synthetic aluminum silicate, magnesium carbonate, precipitated calcium carbonate, magnesium oxide, aluminum hydroxide, and sodium hydrogencarbonate; and pH regulators such as L-arginine, sodium phosphate, disodium hydrogenphosphate, sodium dihydrogenphosphate, potassium phosphate, dipotassium hydrogenphosphate, potassium dihydrogenphosphate, disodium citrate, sodium succinate, ammonium chloride, and sodium benzoate. Of these, preferred are magnesium aluminometasilicate, magnesium aluminosilicate, and L-arginine.

Even more preferred are basic substances that may be added to the pharmaceutical composition comprising NK-104 to control the pH of the composition and that maintain the outward appearance and stability of said composition. These may be any of alkaline earth metal silicates including aluminum, and organic base compounds. For example, alkaline earth metal means magnesium, calcium, barium, etc. Preferred is magnesium. Particularly preferred alkaline earth metal silicates including aluminum are magnesium aluminometasilicate (NEUSILIN FH2), magnesium aluminosilicate (NEUSILIN A), and magnesium aluminum silicate (VEEGUM F). The preferred organic base is arginine. An even more preferred base is L-arginine.

The pharmaceutical composition of the present invention can be formulated into various forms of preparations, but preferred are peroral solid preparations. For example, the composition may be formulated into tablets, granules, powders, troches, capsules, chewables, film-coated preparations of these, and even sugar-coated preparations thereof.

Where the pharmaceutical composition of the present invention is formulated into such peroral solid preparations, any of vehicles (excipients), binders, disintegrators and lubricants can be added thereto, if desired. The preparations may be formulated from the composition along with any of these, in any ordinary manner.

The vehicles (excipients) include, for example, lactose, corn starch, denatured corn starch, mannitol, sorbitol, wood cellulose, fine crystalline cellulose and calcium carbonate, which can be used either singly or as combined.

The binders include, for example, hydroxypropyl cellulose, hydroxypropylmethyl cellulose, polyvinyl pyrrolidone, polyvinyl alcohol, and partial saponificates of these, which can be used either singly or as combined. Especially preferred is hydroxypropylmethyl cellulose.

The disintegrators include, for example, low substituted hydroxypropyl cellulose, carmellose, sodium carboxystarch, calcium carmellose, corn starch, partially-alphatized starch, sodium closcarmellose and clospovidone, which can be used either singly or as combined. Especially preferred is low substituted hydroxypropyl cellulose.

The lubricants includes, for example, magnesium stearate, stearic acid, palmitic acid, calcium stearate and talc, which can be used either singly or as combined.

The amounts of the ingredients constituting the composition of the present invention are not specifically defined. For example, the amount of NK-104 or its salt or ester may be from 0.01 to 40% by weight, preferably from 0.05 to 10% by weight, more preferably from 0.5 to 5% by weight; and the basic substance may be added to the composition in such an amount that is necessary for making the aqueous solution or dispersion of the composition have pH of from 6.8 to less than 8. Where the composition is formulated into peroral solid preparations, it is desirable that the vehicle is added thereto in an amount of from 30 to 95% by weight, the binder in an amount of from 1 to 20% by weight, the disintegrator in an amount of from 1 to 30% by weight, and the lubricant in an amount of from 0.5 to 10% by weight.

If further desired, any additional components, such as sweeteners, flavorings and colorants may also be added to the composition of the present invention.

The necessary amount of the basic substance to be added to the composition of the invention in order to make the aqueous solution or dispersion of the composition have pH of from 6.8 to less than 8 may be from about 1 to 6.5% by weight or so, if magnesium aluminometasilicate (NEUSILIN FH2) is used, from about 0.5 to 2% by weight or so, if magnesium aluminosilicate (NEUSILIN A) is used, from about 2 to 8% by weight or so, if magnesium aluminium silicate (VEEGAM F) is used, or from about 0.01 to 0.1% by weight or so, if L-arginine is used singly. As mentioned above, it is preferable that the basic substance is used singly. However, two or more such basic substances can be used in combination.

The composition of the present invention can be coated to give film-coated tablets or sugar-coated tablets. As the coating base, for example, usable are celluloses such as hydroxypropyl cellulose, hydroxypropylmethyl cellulose; and also aminoalkyl methacrylate copolymer E, white sugar, and pullulan. As the plasticizer for the base, for example, usable are macrogol 6000, triethyl citrate, and triacetylpropylene glycol.

The pharmaceutical composition of the present invention can be produced according to any ordinary methods employable in producing peroral solid preparations. If stirring granulation is employed, this may be conducted as follows. First, NK-104, a basic substance, a vehicle, a binder and a disintegrator are mixed. Next, water is added to the resulting mixture, then granulated with stirring, dried and dressed to give dry granules. Further, the granules are mixed with a lubricant, and pelletized with a pelletizer into pellets. Also employable is fluidized bed granulation, which may be conducted as follows. First, NK-104, a basic substance, a vehicle and a disintegrator are mixed. Then, an aqueous solution of a binder is sprayed over the resulting mixture, using a fluidized bed granulator, to prepare granules. These granules are mixed with a lubricant, and then pelletized with a pelletizer into pellets.

Using ordinary coating devices, the pellets as produced according to the above-mentioned methods can be coated with a solution or suspension comprising a coating base and optionally a plasticizer and a colorant to give film-coated tablets or sugar-coated tablets.

BEST MODES OF CARRYING OUT THE INVENTION

Examples of the pharmaceutical composition of the present invention are mentioned below, which, however, are not intended to restrict the scope of the invention.

Example 1

Decomposition Products of NK-104 and Fluvastatine

Figure 2:
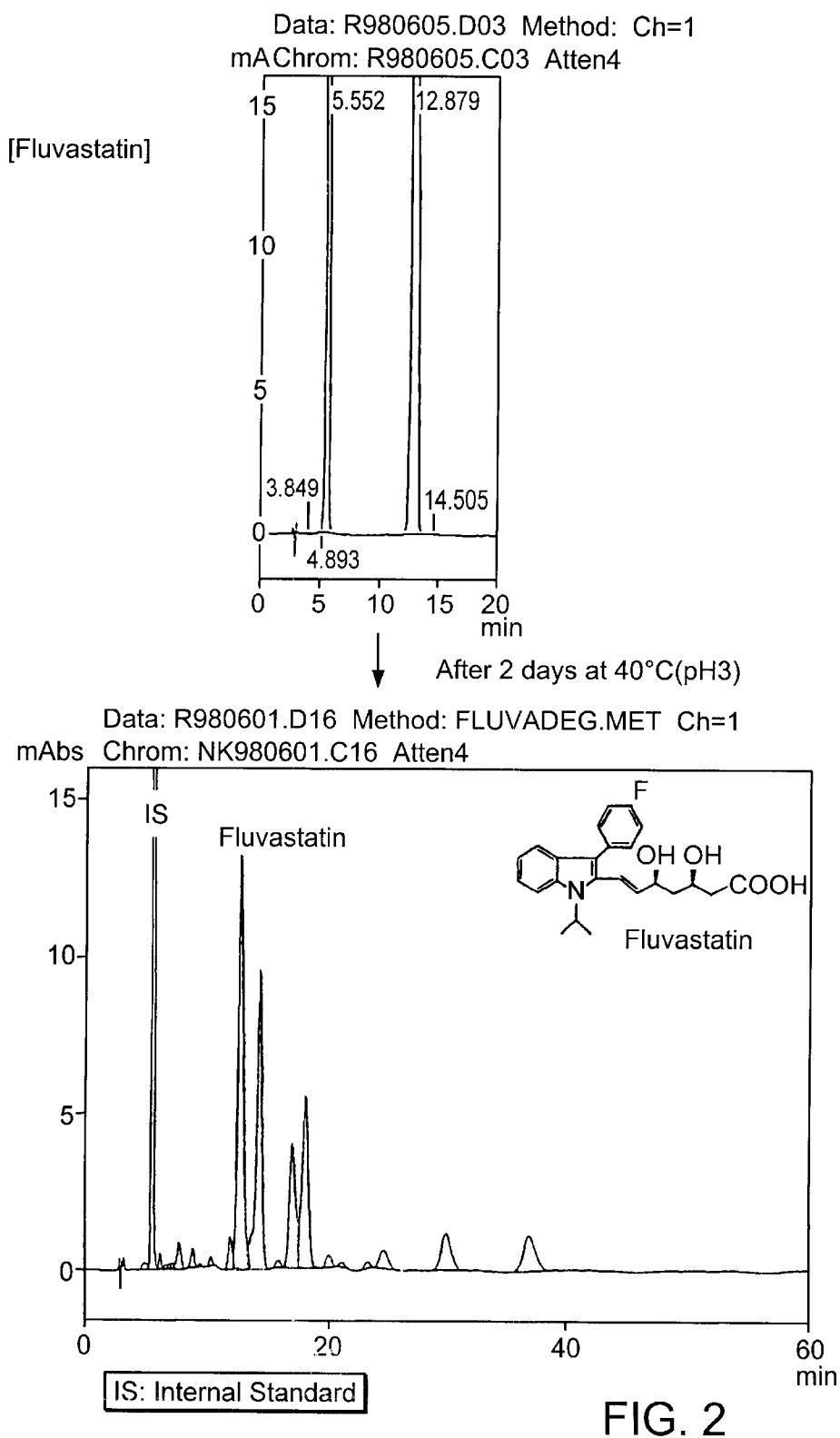
FIG. 2 shows histograms of fluvastatin decomposition products analyzed by HPLC.

Decomposition products of NK-104 were analyzed by HPLC after incubation for two days at 40° C. in aqueous solution of pH 3. NK-104 produced a single product, a lactonized form of NK-104 (see FIG. 1). The decomposition products of fluvastatin were also analyzed for comparison. Fluvastatin produced many types of products, which are believed to include an optical isomer of fluvastatin and a lactonized form of fluvastatin (see FIG. 2).

The conditions under which NK-104 and Fluvastatine decomposition products were analyzed are as follows:

HPLC system: Type LC-10 (Shimadz, Japan)

Column: DEVELOSIL ODS-HG-5 (NOMURA CHEM., Japan)

Mobil Phase: MeOH/0.02 mol/L phosphate buffer (pH 3)=7/3

Sample: NK-104 or fluvastatin/pH 3/40° C., 2 days

Detector: SPD-MLOAVP, UV 245 mm

NK-104 and fluvastatin have common $\alpha$-$\delta$-dihydroxy-$\epsilon$-ene carboxylic acid chemical structure. However, NK-104 and fluvastatin differ in the types and amount of decomposition products. Namely, NK-104 provides a small quantity of one type of decomposition product while fluvastatin provides comparatively large quantities of different types of decomposition products (see FIGS. 1 and 2). Such differences show that stability of each depends not only on the chemical structure of $\alpha$-$\delta$-dihydroxy-$\epsilon$-ene carboxylic acid but also on the chemical structures that are unique to each.

In the following examples, the low substituted hydroxypropyl cellulose was commercially available as sold for a medicine additive and contains from 5–16% of —$OC_3H_6OH$ group. Hydroxypropylmethyl cellulose 2910 contains 28–30% —$OCH_3$ and 7–12% —$OC_3H_6$—OH. Both low substituted hydroxypropyl cellulose and hydroxypropylmethyl cellulose 2910 as used in the examples are described in The Pharmacopoeia of Japan, 12th edition.

Example 2

Herein produced were tablets each having the composition mentioned below.

| | |
|---|---|
| Calcium Salt of NK-104 | 1.0 mg |
| Lactose | 101.4 |
| Low Substituted Hydroxypropyl Cellulose | 12.0 |
| Hydroxypropylmethyl Cellulose 2910 | 2.0 |
| Magnesium Aluminometasilicate | 2.4 |
| Magnesium Stearate | 1.2 |
| Total (one tablet) | 120.0 |

The components of the above-mentioned composition, except magnesium stearate, were mixed to prepare a homogeneous powdery mixture, to which was added a suitable amount of pure water. The resulting mixture was granulated with stirring, and pelletized to give pellets. Magnesium stearate was added to and mixed with these pellets, which were then tabletted into NK-104-containing tablets.

Example 3

In the same manner as in Example 2, herein produced were tablets each having the composition mentioned below.

| | |
|---|---|
| Calcium Salt of NK-104 | 1.0 mg |
| Lactose | 102.8 |
| Low Substituted Hydroxypropyl Cellulose | 12.0 |
| Hydroxypropylmethyl Cellulose 2910 | 2.0 |
| Dipotassium Hydrogenphosphate | 1.0 |
| Magnesium Stearate | 1.2 |
| Total (one tablet) | 120.0 |

Example 4

In the same manner as in Example 2, herein produced were tablets each having the composition mentioned below.

| | |
|---|---|
| Calcium Salt of NK-104 | 1.0 mg |
| Lactose | 103.7 |
| Low Substituted Hydroxypropyl Cellulose | 12.0 |
| Hydroxypropylmethyl Cellulose 2910 | 2.0 |
| L-arginine | 0.1 |
| Magnesium Stearate | 1.2 |
| Total (one tablet) | 120.0 |

Example 5

In the same manner as in Example 2, herein produced were tablets each having the composition mentioned below.

| | |
|---|---|
| Calcium Salt of NK-104 | 1.0 mg |
| Lactose | 103.2 |
| Low Substituted Hydroxypropyl Cellulose | 12.0 |
| Hydroxypropylmethyl Cellulose 2910 | 2.0 |
| Magnesium Aluminometasilicate | 0.6 |
| Magnesium Stearate | 1.2 |
| Total (one tablet) | 120.0 |

TEST 1

The pH of a 5% suspension of tablets produced in any of Examples 2 to 5 (the suspension was prepared by suspending one tablet in 2.4 ml of pure water) was measured.

After having been stored at 60° C. for 2 weeks, the percentage retention of calcium salt of NK-104 in the tablets was measured according to HPLC. After having been stored at 60° C. for 3 days, the change in the outward appearance of the tablets was observed. The test results are shown in Table 1.

TABLE 1

| | Example 2 | Example 3 | Example 4 | Example 5 |
|---|---|---|---|---|
| pH of 5% Suspension | 7.8 | 7.7 | 7.5 | 7.1 |
| Percentage Retention of Ca NK-104 | 97% | 97% | 93% | 92%. |
| Change in Outward Appearance | No change | No change | No change | No change |

Control Examples 1 to 3

In the same manner as in Example 2, herein produced were control tablets each having the composition mentioned below. These tablets were tested in the same manner as in Test 1, to determine the pH of the 5% suspension of each tablet, the percentage retention of Ca NK-104, and the change in the outward appearance of the tablets. The test results are shown in Table 2.

TABLE 2

| | Control Example 1 | Control Example 2 | Control Example 3 |
|---|---|---|---|
| Ca NK-104 | 1.0 mg | 1.0 mg | 1.0 mg |
| Lactose | 103.8 | 98.8 | 98.8 |
| Low Substituted Hydroxypropyl Cellulose | 12.0 | 12.0 | 12.0 |

TABLE 2-continued

|  | Control Example 1 | Control Example 2 | Control Example 3 |
|---|---|---|---|
| Hydroxypropyl Cellulose 2910 | 2.0 | 2.0 | 2.0 |
| Sodium Ascorbate |  | 5.0 |  |
| Ascorbic Acid |  |  | 5.0 |
| Magnesium Stearate | 1.2 |  |  |
| Total (one tablet) | 120.0 | 120.0 | 120.0 |
| pH of 5% Suspension | 6.6 | 6.3 | 3.3 |
| Percentage Retention of Ca NK-104, after stored at 60° C. for 2 weeks | 88% | 77% | 38% |
| Change in Outward Appearance, after stored at 60° C. for 3 days | No change | No change | No change |

As in Tables 1 and 2 showing the test results, it is obvious that the percentage retention of Ca NK-104 in the 5% suspension of the composition having pH of 7 or higher is high, after having been stored at 60° C. for 2 weeks, while the same in the 5% suspension thereof having pH of lower than 6.6 becomes lower with the decrease in the pH value thereof.

Example 6 and Control Example 4

In the same manner as in Example 2, herein produced were tablets each having the composition mentioned below. These tablets were tested in the same manner as in Test 1, to determine the pH of the 5% suspension of each tablet, and the change in the outward appearance of the tablets. The test results are shown in Table 3.

TABLE 3

|  | Example 6 | Control Example 4 |
|---|---|---|
| Ca NK-104 | 1.0 mg | 1.0 mg |
| Lactose | 101.4 | 93.9 |
| Low Substituted Hydroxypropyl Cellulose | 12.0 | 12.0 |
| Hydroxypropylmethyl Cellulose 2910 | 2.0 | 2.0 |
| Magnesium Aluminometasilicate | 2.4 | 9.9 |
| Magnesium Stearate | 1.2 | 1.2 |
| Total (one tablet) | 120.0 | 120.0 |
| pH of 5% Suspension | 7.8 | 8.3 |
| Change in Outward Appearance, after stored at 60° C. for 3 days | No change | Changed to pale yellowish brown |

Example 7 and Control Examples 5 and 6

In the same manner as in Example 2, herein produced were tablets each having the composition mentioned below. These tablets were tested in the same manner as in Test 1, to determine the pH of the 5% suspension of each tablet, and the change in the outward appearance of the tablets. The test results are shown in Table 4.

TABLE 4

|  | Example 7 | Control Example 5 | Control Example 6 |
|---|---|---|---|
| Ca NK-104 | 1.0 mg | 1.0 mg | 1.0 mg |
| Lactose | 103.7 | 95.8 | 93.9 |
| Low Substituted Hydroxypropyl Cellulose | 12.0 | 12.0 | 12.0 |
| Hydroxypropylmethyl Cellulose 2910 | 2.0 | — | 2.0 |
| TC-5R | — | 2.0 | — |
| L-arginine | 0.1 | 8.0 | 9.9 |

TABLE 4-continued

|  | Example 7 | Control Example 5 | Control Example 6 |
|---|---|---|---|
| Magnesium Stearate | 1.2 | 1.2 | 1.2 |
| Total (one tablet) | 120.0 | 120.0 | 120.0 |
| pH of 5% Suspension | 7.5 | 9.3 | 9.8 |
| NK-104 remaining (%) after 2 weeks at 60° C. | 93.4 | 66.0 | — |
| Change in Outward Appearance, after 2 weeks at 60° C. | No change | Changed to brown | — |
| Change in Outward Appearance, after stored at 60° C. for 3 days | — | — | Changed to pale yellowish green |

Example 8 and Control Example 7

In the same manner as in Example 2, herein produced were tablets each having the composition mentioned below. These tablets were tested in the same manner as in Test 1, to determine the pH of the 5% suspension of each tablet, and the change in the outward appearance of the tablets. The test results are shown in Table 5.

TABLE 5

|  | Example 8 | Control Example 7 |
|---|---|---|
| Ca NK-104 | 1.0 mg | 1.0 mg |
| Lactose | 101.8 | 93.9 |
| Low Substituted Hydroxypropyl Cellulose | 12.0 | 12.0 |
| Hydroxypropylmethyl Cellulose 2910 | 2.0 | 2.0 |
| Sodium Hydrogencarbonate | 2.0 | 9.9 |
| Magnesium Stearate | 1.2 | 1.2 |
| Total (one tablet) | 120.0 | 120.0 |
| pH of 5% Suspension | 7.8. | 9.8 |
| Change in Outward Appearance, after stored at 60° C. for 3 days | No change | Changed to dark navy blue |

Example 9 and Control Example 8

In the same manner as in Example 2, herein produced were tablets each having the composition mentioned below. These tablets were tested in the same manner as in Test 1, to determine the pH of the 5% suspension of each tablet, and the change in the outward appearance of the tablets. The test results are shown in Table 6.

TABLE 6

|  | Example 9 | Control Example 8 |
|---|---|---|
| Ca NK-104 | 1.0 mg | 1.0 mg |
| Lactose | 102.8 | 93.9 |
| Low substituted Hydroxypropyl Cellulose | 12.0 | 12.0 |
| Hydroxypropylmethyl Cellulose 2910 | 2.0 | 2.0 |
| Dipotassium Hydrogenphosphate | 1.0 | 9.9 |
| Magnesium Stearate | 1.2 | 1.2 |
| Total (one tablet) | 120.0 | 120.0 |
| pH of 5% Suspension | 7.7 | 8.4 |
| Change in Outward Appearance, after stored at 60° C. for 3 days | No change | Changed to orange |

As is obvious from the test results in Tables 3 to 6, no change in the outward appearance of the tablets was found when the 5% suspensions of the tablets had pH of 8 or lower, even after having been stored at 60° C. for 3 days, but the outward appearance of the tablets changed when the 5% suspensions of the tablets had pH of higher than 8.

Example 10

Magnesium Aluminometasilicate

In the same manner as in Example 2, herein produced were tablets each having the composition mentioned below. The tablets were tested in the same manner as in Test 1 to determine the pH of the 5% suspension of each tablet, but the percentage retention of Ca NK-104 and the change in outward appearance of the tablets were observed one month after storing at 60° C. The test results are shown in Table 7.

TABLE 7

| | 1 | 2 | 3 | 4 | 5 |
|---|---|---|---|---|---|
| Ca NK-104 | 1.0 mg | 1.0 mg | 1.0 mg | 1.0 mg | 1.0 mg |
| Lactose | 101.4 | 100.8 | 91.8 | 53.8 | 0 |
| Low substituted Hydroxypropyl Cellulose | 12.0 | 12.0 | 12.0 | 12.0 | 12.0 |
| Hydroxypropylmethyl Cellulose 2910 | 2.0 | 2.0 | 2.0 | 2.0 | 2.0 |
| Magnesium Aluminometasilicate | 2.4 | 3.0 | 12.0 | 50.0 | 103.8 |
| Magnesium Stearate | 1.2 | 1.2 | 1.2 | 1.2 | 1.2 |
| Total (one tablet) | 120.0 | 120.0 | 120.0 | 120.0 | 120.0 |
| pH of 5% Suspension | 7.8 | 8.1 | 8.4 | 9.0 | 9.3 |
| NK-104 remaining rate (%) after 1 month at 60° C. | 97.4 | 96.5 | 92.2 | 84.5 | 69.1 |
| Change in Outward Appearance, after stored at 60° C. for 1 month | No change | Pale yellow | Pale yellow | Pale yellow | No change |

Example 11

Magnesium Aluminosilicate

In the same manner as in Example 2, herein produced were tablets each having the composition mentioned below. The tablets were tested in the same manner as in Test 1 to determine the pH of the 5% suspension of each tablet, but the percentage retention of Ca NK-104 was observed at both 2 weeks and one month after storing at 60° C. and the change in outward appearance of the tablets was observed one month after storing at 60° C. The test results are shown in Table 8.

TABLE 8

| | 1 | 2 | 3 | 4 | 5 |
|---|---|---|---|---|---|
| Ca NK-104 | 1.0 mg | 1.0 mg | 1.0 mg | 1.0 mg | 1.0 mg |
| Lactose | 103.2 | 102.6 | 101.8 | 98.8 | 96.8 |
| Low substituted Hydroxypropyl Cellulose | 12.0 | 12.0 | 12.0 | 12.0 | 12.0 |
| Hydroxypropylmethyl Cellulose 2910 | 2.0 | 2.0 | 2.0 | 2.0 | 2.0 |
| Magnesium Aluminosilicate | 0.6 | 1.2 | 2.0 | 5.0 | 7.0 |
| Magnesium Stearate | 1.2 | 1.2 | 1.2 | 1.2 | 1.2 |
| Total (one tablet) | 120.0 | 120.0 | 120.0 | 120.0 | 120.0 |
| pH of 5% Suspension | 6.8 | 7.8 | 8.1 | 8.4 | 8.7 |
| NK-104 remaining rate (%) after two weeks at 60° C. | 97.3 | 98.5 | 91.7 | 87.4 | 86.8 |
| NK-104 remaining rate (%) after 1 month at 60° C. | 97.5 | 93.5 | 87.2 | 80.7 | 79.1 |
| Change in Outward Appearance, after stored at 60° C. for 1 month | No change | No change | No change | No change | No change |

Example 12

Magnesium Aluminum XSilicate

In the same manner as in Example 2, herein produced were tablets each having the composition mentioned below. The tablets were tested in the same manner as in Test 1 to determine the pH of the 5% suspension of each tablet, but the percentage retention of Ca NK-104 and the change in outward appearance of the tablets were observed one month after storing at 60° C. The test results are shown in Table 9.

TABLE 9

| | 1 | 2 | 3 | 4 | 5 |
|---|---|---|---|---|---|
| Ca NK-104 | 1.0 mg | 1.0 mg | 1.0 mg | 1.0 mg | 1.0 mg |
| Lactose | 100.2 | 99.4 | 97.8 | 91.8 | 43.8 |
| Low substituted Hydroxypropyl Cellulose | 12.0 | 12.0 | 12.0 | 12.0 | 12.0 |
| Hydroxypropylmethyl Cellulose 2910 | 2.0 | 2.0 | 2.0 | 2.0 | 2.0 |
| Magnesium Aluminum Silicate | 3.6 | 4.4 | 6.0 | 12.0 | 60.0 |
| Magnesium Stearate | 1.2 | 1.2 | 1.2 | 1.2 | 1.2 |
| Total (one tablet) | 120.0 | 120.0 | 120.0 | 120.0 | 120.0 |
| pH of 5% Suspension | 7.5 | 8.2 | 8.7 | 9.1 | 9.7 |
| NK-104 remaining rate (%) after 1 month at 60° C. | 97.7 | 98.8 | 98.2 | 92.5 | 84.3 |
| Change in Outward Appearance, after stored at 60° C. for 1 month | No change | No change | Pale yellow | Pale gray | Gray |

INDUSTRIAL APPLICABILITY OF THE INVENTION

The pharmaceutical composition of the present invention has good time-dependent stability, with having no change in the outward appearance thereof even after having been stored long. Therefore, the composition is good in medical use, especially in the form of peroral solid preparations.

The pharmaceutical compositions of the present invention that contains NK-104 or salt or ester thereof are especially useful for treating a patient, particularly a human, that is suffering from or susceptible to hyperlipemia or atherosclerosis by administering the pharmaceutical composition to such patient.

Particularly preferred unit dosages have been described in the examples above. It will be appreciated the specifically preferred dosage amounts of a pharmaceutical composition of the invention used in a given therapy will vary according to various known factors such as the particular compositions formulated, the specific compound utilized, the mode of application, the particular site of administration, etc. Optimal administration rates for a given protocol of administration can be readily ascertained by those skilled in the art using conventional dosage determination tests conducted with regard to the foregoing guidelines.

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A pharmaceutical composition comprising (E)-3,5-dihydroxy-7-[4'-4"-flurophenyl-2'-cyclopropyl-quinolin-3'-yl]-6-heptenoic acid, or its salt or ester, and a pharmaceutically acceptable carrier, of which an aqueous solution or dispersion of the pharmaceutical composition has pH of from 6.8 to 7.8.

2. The pharmaceutical composition as claimed in claim 1, wherein the salt of (E)-3,5-dihydroxy-7-[4'-4"-fluorophenyl-2'-cyclopropyl-quinolin-3'-yl]-6-heptenoic acid is a calcium salt of the acid.

3. The pharmaceutical composition of claim 1 wherein the composition further comprises a basic substance.

4. The pharmaceutical composition of claim 3 wherein the basic substance is an organic base compound.

5. The pharmaceutical composition of claim 3 wherein the basic substance is an alkaline earth metal silicate.

6. The pharmaceutical composition of claim 5 wherein the basic substance is an aluminum compound.

7. The pharmaceutical composition of claim 5 wherein the alkaline earth metal silicate is a magnesium salt.

8. The pharmaceutical composition of claim 3 wherein the basic substance is one or more selected from magnesium aluminometasilicate, magnesium aluminosilicate and magnesium aluminum silicate.

9. The pharmaceutical composition of claim 3 wherein the basic substance is L-arginie.

10. The pharmaceutical composition of claim 3 wherein the composition further comprises at least one material selected from the group consisting of vehicles, disintegrators, binders and lubricants.

11. The pharmaceutical composition of claim 3 wherein the composition further comprises a peroral solid preparation.

12. The pharmaceutical composition of claim 3 wherein the composition further comprises a lactose vehicle.

13. The pharmaceutical composition of claim 3 wherein the composition further comprises hydroxypropyl cellulose with a low degree of substitution.

14. The pharmaceutical composition of claim 3 wherein the composition further comprises a binder of hydroxy propylmethyl cellulose.

15. The pharmaceutical composition of claim 1 wherein the composition further comprises at least one material selected from the group consisting of vehicles, disintegrators, binders and lubricants.

* * * * *